United States Patent [19]

Apple et al.

[11] 4,331,156
[45] May 25, 1982

[54] ESOPHAGEAL CARDIAC PULSE MONITORING APPARATUS AND METHOD

[75] Inventors: Howard P. Apple; Paul J. Dauchot, both of Cleveland Heights, Ohio

[73] Assignee: University Patents, Inc., Norwalk, Conn.

[21] Appl. No.: 134,819

[22] Filed: Mar. 28, 1980

[51] Int. Cl.³ .............................................. A61B 5/02
[52] U.S. Cl. .................................... 128/688; 128/715
[58] Field of Search ............... 128/671, 673, 675, 687, 128/688, 689, 695, 715, 748

[56] References Cited

U.S. PATENT DOCUMENTS

| | | | |
|---|---|---|---|
| 2,949,910 | 8/1960 | Brown et al. | 128/715 |
| 3,052,756 | 9/1962 | Seven et al. | 128/715 |
| 3,171,406 | 3/1965 | Baum et al. | 128/715 |
| 3,499,435 | 3/1970 | Rockwell et al. | 128/715 |
| 3,951,136 | 4/1976 | Wall | 128/715 |
| 4,214,593 | 7/1980 | Imbruce et al. | 128/748 |
| 4,252,126 | 2/1981 | Mandi | 128/675 |

OTHER PUBLICATIONS

Shaw et al., "Medical and Biological Engineering" vol. 18, No. 4, Jul., 1980, pp. 488–492.

*Primary Examiner*—William E. Kamm
*Attorney, Agent, or Firm*—Pollock, Vande Sande & Priddy

[57] ABSTRACT

An esophageal cardiac pulse probe includes a lumen for insertion into the esophagus, the end of the lumen preferably being closed by a flexible diaphragm. Pressure variations imparted to the fluid within the lumen in response to sounds from the heart and the lungs are transmitted to an electrical transducer which produces an electrical signal proportional to the time-varying frequency and intensity of the pressure variations. This signal is selectively filtered to effectively eliminate signal components due to respiratory noise and audible heart sounds and the resulting signal is fed to an appropriate visual display apparatus. Direct acoustic cardiac sound monitoring is also achievable with an earpiece connected to the lumen. Several probe geometries and a method of cardiac pulse waveform monitoring are also disclosed.

25 Claims, 6 Drawing Figures

ESOPHAGEAL CARDIAC PULSE MONITORING APPARATUS AND METHOD

DESCRIPTION

TECHNICAL FIELD

The present invention relates in general to devices and methods for monitoring the cardiac pulse. More particularly, the invention concerns esophageal stethoscopes and devices and techniques for monitoring the cardiac pulse waveform using such stethoscopes.

BACKGROUND ART

Esophageal stethoscopes were first described nearly three decades ago and have been in clinical use during anesthesia since then to enable the anesthesiologist to obtain a rather direct acoustic measure of the heart's performance. Such acoustic esophageal stethoscopes typically have comprised a tube or lumen which is inserted into the patient's esophagus to a location at which pressure variations due to heart and respiratory sounds are best transmitted to the interior of the lumen, by means such as a flexible diaphragm. The anesthesiologist is provided with an earpiece connected to the lumen by a suitable conduit, so that an acoustic indication of heart activity is provided. In some instances rather than an acoustic earpiece, the stethoscope has been provided with an electro-mechanical transducer, such as a piezo-electrical device, which produces a signal proportional to pressure variations in the lumen, the signal then being provided directly to a speaker or headset following amplification. In either case, determination of the actual cardiac pulse waveform, which is monitored for various reasons during surgery, has not been attempted via the esophageal stethoscope. Rather, external pressure transducers applied to the carotid artery or electro-optical transducers applied to the fingers have been relied on to determine cardiac pulse waveform. For many reasons, these external devices are either not useful on certain patients or are somewhat unreliable. Thus, a need has continued to exist for a simple, reliable cardiac pulse monitor which can be used on most patients while they are under anesthesia.

DISCLOSURE OF THE INVENTION

A primary object of the invention is to provide an improved esophageal stethoscope which can be used on most patients to provide an indication of cardiac pulse waveform.

Another object of the invention is to provide such a stethoscope which also will provide a direct, acoustic indication of heart sounds.

A further object of the invention is to provide such a stethoscope in which cardiac pulse waveform and acoustic indication of heart sounds are determined in isolated portions of the stethoscope probe.

Still another object of the invention is to provide such a stethoscope which produces an electrical signal proportional to cardiac pulse waveform, and includes means for conveying the signal to existing signal display devices such as oscilloscopes and strip chart recorders.

Yet another object of the invention is to provide such a stethoscope which produces an electrical signal proportional to cardiac waveform, the signal being free of high frequency components primarily due to heart noises and low frequency components primarily due to respiratory noises.

A still further object of the invention is to provide a method of monitoring cardiac pulse wave form using an esophageal lumen.

These objects of the invention are given only by way of example; thus, other desirable objectives and advantages inherently achieved by the disclosed invention may occur to those skilled in the art. Nonetheless, the scope of the invention is to be limited only by the appended claims. One aspect of the invention concerns an improved method of determining the cardiac pulse waveform by monitoring pressure variations in the esophagus. Means, such as a lumen, are used to convey these variations to an electro-mechanical transducer which produces an output signal proportional to the frequency and intensity of the pressure variations. By filtering out low frequency components attributable mainly to respiratory noises and higher frequency components attributable mainly to heart noises, a sub-audible signal is obtained which is proportional to the cardiac pulse waveform. The sub-audible signal proportional to the cardiac pulse waveform has been found to be in the range of 0.1 to 30 Hz.

The probe used to convey pressure variations to the transducer may be configured in several ways. A simple, open-ended lumen can be used; however, its reliability is uncertain since liquids in the esophagus may block the open end and prevent transmission of pressure variations up the lumen to the transducer. Improved performance is achieved if the single lumen is provided with radially extending holes adjacent its lower end and a flexible, cuff-like or tubular diaphragm surrounding and spaced from the lumen in the vicinity of the holes. The diaphragm then expands upon internal application of fluid pressure to just touch the walls of the esophagus. This probe is similar to that used in the past for simple acoustic monitoring. Direct acoustic monitoring of heart sounds also is achievable using an acoustic earpiece connected to the single lumen; however, an isolation diaphragm should be included in the earpiece to prevent leakage.

In the preferred probe according to the invention, two lumens are used, one located within the other. The outer lumen is relatively flexible and the inner one is considerably smaller and relatively stiff. At their lower ends, the two lumens are isolated from each other by a seal extending between them. The outer lumen is provided with radially extending holes below the location of the seal. A tubular diaphragm similar to that just mentioned surrounds and is spaced from the outer lumen in the vicinity of the holes, so that pressure variations in the esophagus are transmitted to the inner lumen and from there to the transducer. Where direct acoustic monitoring is also desired, the seal between the lumens is located between the ends of that portion of the outer lumen in which the holes have been provided; and the diaphragm is provided with a reduced diameter portion which engages the outer lumen in the vicinity of the seal. Thus, pressure variations in the esophagus are transmitted to both the inner lumen and the space between the inner and the outer lumens. The transducer again is connected to the inner lumen and an acoustic earpiece is connected to the outer lumen. In this instance, an isolation diaphragm is not needed in the earpiece. Although the arrangement is not optimum, parallel single lumens may also be used, each having an associated diaphragm at its lower end, one being connected to the transducer and one being connected to an acoustic earpiece.

The signal processing circuitry according to the invention is simple and reliable. The piezoelectric transducers which are preferred in the invention have a certain inherent capacitance. When the output signal of the transducer is fed to a buffer amplifier having a suitably high impedance, the resultant effect is to filter out certain low frequency components. In accordance with the invention, components below about 0.1 Hz are filtered out, since they are attributable primarily to respiratory noises, sometimes referred to as the respiration artifact. Applicants have found that by further filtering the amplifier output to eliminate components above approximately 30 Hz, a sub-audible signal proportional to cardiac pulse waveform is obtained. The amplifier output may also be filtered to provide an audible signal proportional to heart sounds. By gating the signal proportional to pulse waveform at a preselected point in the output from a conventional electrocardiogram machine, synchronized display of the two signals may be achieved on an oscilloscope or a strip chart recorder.

BEST MODE FOR CARRYING OUT THE INVENTION

Figure 1:
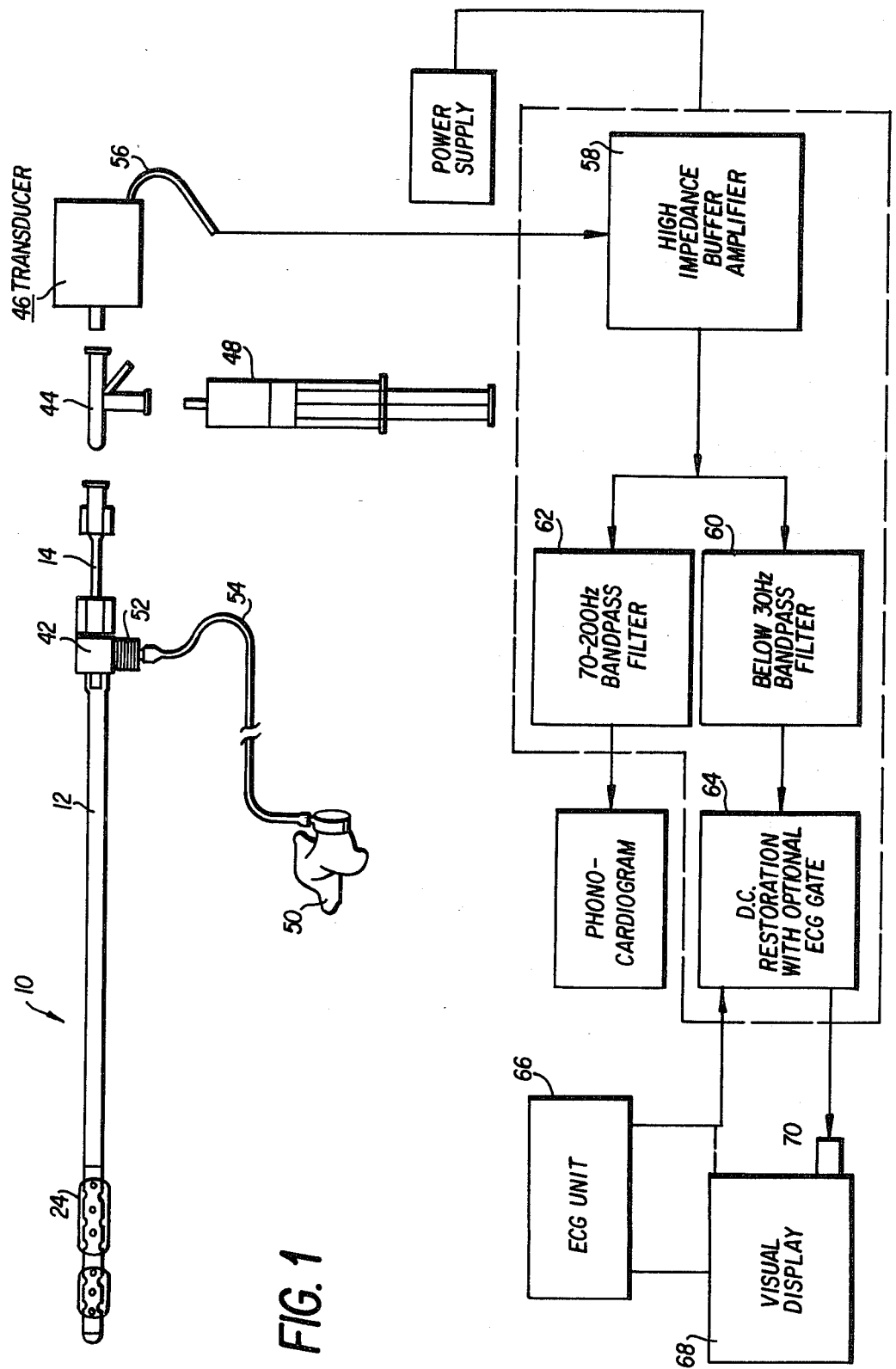
FIG. 1 shows a schematic, partially exploded view of an esophageal cardiac pulse monitoring apparatus according to the invention.

The invention will be described with reference to the drawings, in which like reference numerals identify like elements of structure in each of the several figures.

Figure 2:
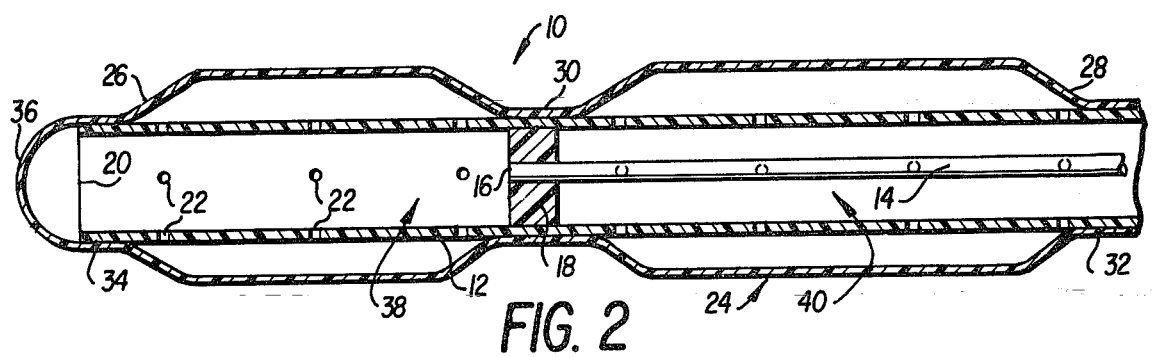
FIG. 2 shows an enlarged, sectional view of an esophageal probe used in the apparatus shown in FIG. 1.

Referring to FIGS. 1 and 2, the cardiac pulse monitoring apparatus according to the invention is seen to comprise an esophageal probe 10 which is assembled from an outer tube or lumen 12 and an essentially concentric inner lumen 14. Lumen 12 is preferably 4 mm to 8 mm in outer diameter and 3 to 5 mm in inner diameter; whereas, lumen 14 is preferably 2 to 3 mm in outer diameter and 1 to 2 mm in inner diameter. To optimize gain and frequency response, the internal volume of lumen 14 preferably is in the range of 0.5 to 3 cc. For lumens made from the preferred vinyl tubing, lumen 14 is comparatively stiffer than lumen 12, which makes lumen 14 less sensitive to pressure variations acting on its walls. Concentric lumen 12 is more compliant to the shape of the esophagus, and also protects lumen 14 from some pressure variations that could pass through its walls, as well as undesirable contact with adjacent body elements or hardware. The lower end 16 of lumen 14 extends through a seal block or fitting 18 which preferably is sealed to both lumens by means such as a suitable glue. Lumen 12 extends past seal block 18 to its lower end 20 and on either side of seal block 18 is provided with a plurality of radially extending holes 22 about its circumference and along a portion of its length. A tubular diaphragm or balloon 24 extends along and surrounds the portion of lumen 12 in which holes 22 are located. To maintain a radial spacing between diaphragm 24 and lumen 12, the diaphragm includes radially extending shoulder portions 26, 28 projecting inwardly at its opposite ends and a reduced diameter portion 30 engaging lumen 12 in the region where seal block 18 is located. A cuff 32 extends upward along lumen 12 from shoulder portion 28; and a cuff 34 and spherical end closure 36 extend downward along lumen 12 from shoulder portion 26. Diaphragm 24 is formed using conventional techniques from thin vinyl having a wall thickness of about 0.015 to 0.025 cm, and has a maximum diameter in the range of 5.8 to 12.2 mm.

Cuff 32 preferably is glued to the exterior of lumen 12; however, reduced diameter portion 30 preferably engages lumen 12 with a simple tight fit, for purposes to be described subsequently.

As shown in FIG. 2, diaphragm 24 and seal block 18 cooperate with lumens 12 and 14 to define a lower pressure responsive volume 38 and an upper pressure sensing volume 40, each responsive to pressure variations in the esophagus and each isolated from the other. In one actual embodiment, volume 40 was approximately 2.54 cm in length and volume 38 was approximately 1.91 cm in length. Volume 38 communicates with the interior passage of lumen 14; and volume 40, with the annulus between the two lumens. Lumen 14 is led out of probe 10 through a suitable fitting 42 which is inserted into the upper end of lumen 12. A three-way stop cock 44 is attached to the end of lumen 14 at one of the stop cock's ports and to electromechanical transducer 46 at another of its ports. The remaining port of stop cock 44 is adapted to receive the delivery conduit of a simple syringe 48. Fitting 42 also connects the annulus between lumens 12 and 14 to an acoustic earpiece 50, via an expansion bellows 52 and conduit 54. In use, syringe 48 is used to inject a small amount of air into lumen 14, such as approximately 3 cc, so that diaphragm 24 is certain to expand into light contact with the wall of the esophagus and yet to remain compliant.

If excess air is injected into lumen 14 or lumen 14 becomes overpressurized for any reason, leakage from volume 38 into volume 40 past reduced diameter portion 30 will relieve the overpressure. To facilitate this pressure relief, the tightness of portion 30 around lumen 12 may be adjusted as desired by appropriate selection of the inner diameter of diaphragm 24 at portion 30.

The probe is inserted into the patient's esophagus prior to inflation of diaphragm 24 where it surrounds volume 38. The depth of insertion should be at least to the point where the aorta crosses the esophagus; however, experience has shown that better results are achieved when the lower portion of diaphragm is positioned where the left ventricle of the heart is closest to the esophagus. Following inflation, pressure variations are transmitted up lumen 14 to transducer 46, which preferably is a piezoelectric transducer such as the Model 1010C made by Transmed Scientific of San Luis Obispo, Calif. Transducer 46 thus produces an electrical signal on line 56 which is proportional to the varying frequency and intensity of the pressure variations in the esophagus. These signals are fed to the input of a high impedance buffer amplifier 58 which is selected so that its input impedance is high enough, in view of the inherent capacitance of the transducer, effectively to filter out certain low frequency components of the signal, particularly those below about 0.1 Hz. Applicants have found that components below this level are attributable primarily to respiratory noises and may be ignored when determining cardiac pulse waveform. The output from amplifier 58 is fed in parallel to a low band pass filter 60 and a high band pass filter 62. Filter 60 is chosen to pass components of the signal below approximately 30 Hz. The resultant sub-audible signal has components in the 0.1 to 30 Hz range and has been found by applicants to be proportional to the desired cardiac pulse waveform. This signal is fed to a conventional D.C. restoration circuit 64 which may include an optional gating feature controlled by the occurrence of a preselected portion of the output of a conventional electrocardiogram unit 66. The output signals from both the esophageal stethoscope according to the invention and the electrocardiogram unit 66 thus may be synchronized as desired prior to visual presentation on a visual display unit 68, such as an oscilloscope, strip chart recorder or both. Preferably, the apparatus according to the invention is provided with a connector plug 70 for conveying its output signal to display unit 68, via an input socket also intended for carotid artery pulse monitors or electro-optical pulse monitors. Synchronization between the cardiac pulse wave form produced by the invention and the electrocardiogram waveform may be done in visual display unit 68, if desired.

The output from band pass filter 62 is limited to components in the audible 70 to 200 Hz range and is passed to means such as a phonocardiogram 72 which provides an audio output of actual heart sounds, in the known manner.

Figure 3:
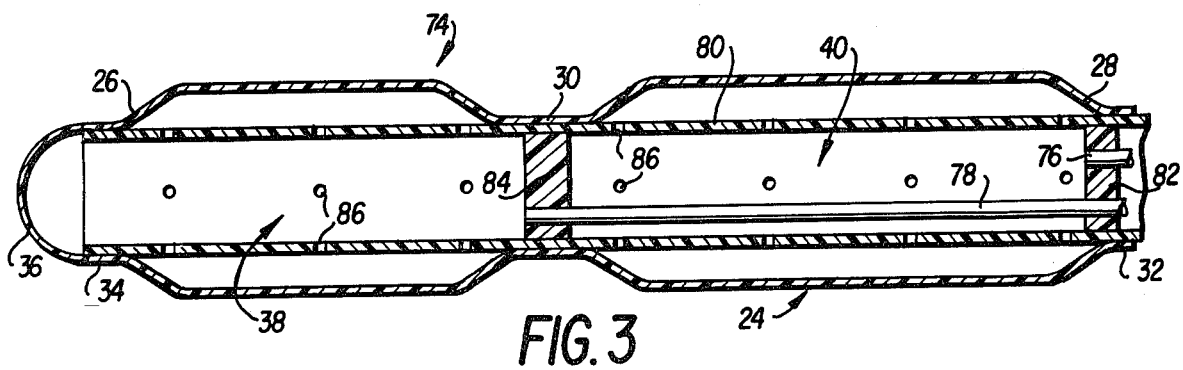

FIG. 3 shows an alternate esophageal stethoscope probe 74 according to the invention. Here, a pair of lumens 76, 78 are fed in parallel to the lower portion of the probe where they enter a third tubular section or lumen 80. Lumen 80 may also extend to the upper end of the probe to simplify handling and protect lumens 76, 78. An upper seal block 82 extends between lumens 76, 78 and the inner wall of lumen 80. Lumen 76 extends just through seal block 82; whereas, lumen 78 extends on through a further seal block 84 located between the ends of lumen 80. A plurality of radially extending holes 86 are provided in lumen 80 on either side of seal block 84, the holes extending about the circumference of lumen 80 and along the portion of its length below seal block 82. A tubular diaphragm 24 surrounds the portion of lumen 80 in which the holes 86 are located, in the manner previously described with respect to FIG. 2. In use, lumen 78 is connected to earpiece 50; and lumen 76, to transducer 46.

Figure 4:
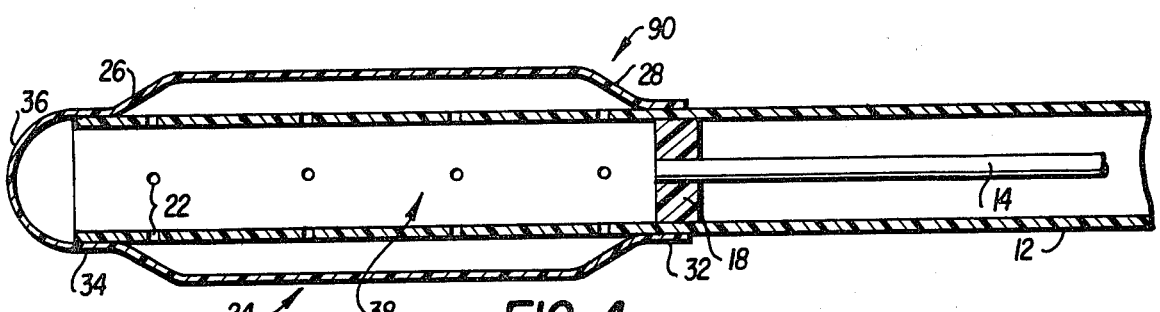
FIGS. 3, 4 and 5 show enlarged sectional views of alternate forms of esophageal probes useful in the apparatus shown in FIG. 1.

FIG. 4 shows another esophageal stethoscope probe 90 according to the invention. In this case, only pressure esponsive volume 38 is provided which is connected to lumen 14. Direct acoustic transmissions of heart sounds are not monitored with this probe since the annulus between lumens 12 and 14 does not communicate with tubular diaphragm 24. Otherwise, the probe is used just as in the case of the embodiments of FIGS. 2 and 3.

Figure 5:
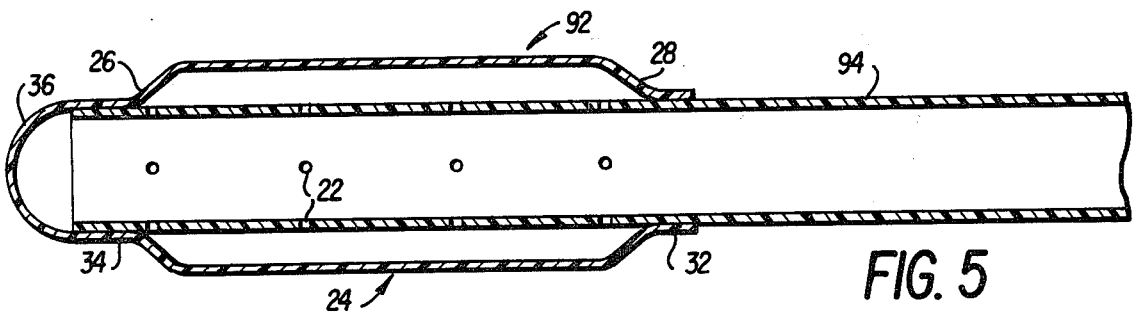
Figure 6:
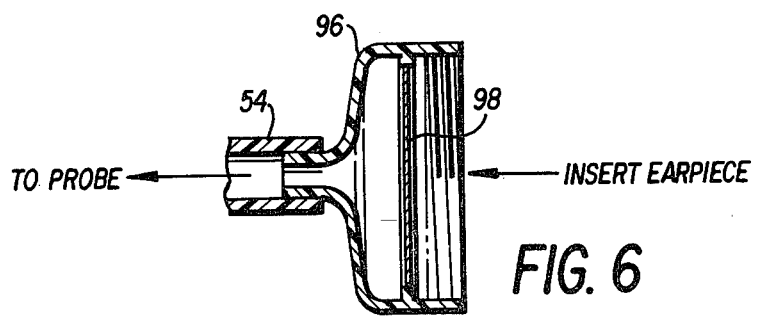
FIG. 6 shows an adapter with an isolation diaphragm which is used to prevent leakage past the acoustic earpiece.

FIG. 5 shows yet another esophageal probe 92 which may be used in accordance with the invention. In this case, all pressure variations to be monitored either electronically or acoustically are conveyed upward from the esophagus through a single lumen 94. To prevent leakage of air through earpiece 50, an adapter 96 is inserted in conduit 54, which includes a hermetically sealed isolation diaphragm 98 as shown in FIG. 6. Pressure variations in conduit 54 thus cause diaphragm 98 to vibrate and transmit the variations to the doctor's ear, without allowing diaphragm 24 to depressurize.

COMMERCIAL APPLICABILITY

The invention is disclosed for use in esophageal stethoscopes in which a gas is used as the pressure transmitting medium. Those skilled in the art will appreciate, however, that a liquid could be used to transmit pressure variations, particularly through lumen 14 to transducer 46, without departing from the scope of the invention.

Having described our invention in sufficient detail to enable those skilled in the art to make and use it, we claim:

1. An improved probe apparatus for an esophageal stethoscope, comprising:
   at least one flexible lumen adapted for insertion into the human esophagus, whereby pressure variations transmitted to the esophagus from the lungs and the heart are transmitted through said at least one lumen to a point outside the body;
   transducer means operatively associated with said at least one lumen and responsive to said pressure variations for producing an electrical signal proportional to the varying frequency and intensity of said pressure variations;
   signal processing means connected to said transducer means for filtering from said electrical signal low frequency components attributable to respiratory noises from the lungs and higher frequency components attributable to heart noises and thereby producing a further sub-audible signal proportional to the cardiac pulse waveform;
   a source of electrical power operatively connected to said signal processing means; and
   means for conveying said further signal to a signal display apparatus.

2. A probe apparatus according to claim 1, wherein there are two lumens, an inner lumen arranged within an outer lumen, said transducer means being responsive to pressure variations transmitted through said inner lumen, further comprising:
   at least one earpiece;
   means for conveying to said at least one earpiece pressure variations transmitted through said outer lumen; and
   flexible diaphragm means for closing the end of at lest one of said two lumens which is to be inserted into the esophagus.

3. A probe apparatus according to claim 2, wherein said flexible diaphragm means closes the ends of both of said lumens which are to be inserted into the esophagus.

4. A probe apparatus according to claim 3, further comprising means for applying a fluid pressure within said inner lumen.

5. A probe apparatus according to claim 2, further comprising means for applying a fluid pressure within the at least one of said two lumens which is closed by said flexible diaphragm means.

6. A probe apparatus according to claim 2, wherein said at least one of said two lumens comprises a plurality of radially extending holes spaced about its circumference at said end to be inserted into the esophagus; and said diaphragm means comprises a tubular portion extending along and surrounding said at least one lumen at the location of said holes, a pair of radially extending shoulder portions, projecting inwardly from the opposite ends of said tubular portion, whereby said tubular portion is radially spaced from said at least one lumen in the vicinity of said holes, and means for attaching said diaphragm to said at least one lumen.

7. A probe apparatus according to claim 2, wherein said outer lumen comprises a plurality of radially extending holes spaced about its circumference and along a portion of its length in the region of the the end of said inner lumen which is to be inserted into the esophagus; further comprising seal means extending between said inner lumen and said outer lumen at a location between the ends of said portion of said outer lumen; and said diaphragm means comprises a tubular portion extending along and surrounding said outer lumen at the location of said holes, said tubular portion having a reduced diameter portion engaging said outer lumen in the region of said seal means and a pair of radially extending shoulder portions projecting inwardly from the opposite ends of said tubular portion, whereby said tubular portion is radially spaced from said outer lumen between said reduced diameter portion and said opposite ends, and means for attaching said diaphragm to said outer lumen.

8. A probe apparatus according to claim 1, wherein there are two flexible lumens, said transducer means being responsive to sound transmitted through one of said two lumens, further comprising:
at least one earpiece;
means for conveying to said at least one earpiece pressure variations transmitted through the other of said two lumens; and
flexible diaphragm means for closing the end of at least one of said two lumens which is to be inserted into the esophagus.

9. A probe apparatus according to claim 8, wherein said flexible diaphragm means closes the ends of both of said lumens which are to be inserted into the esophagus.

10. A probe apparatus according to claim 8, further comprising means for applying a fluid pressure within said one lumen.

11. A probe apparatus according to claim 8, further comprising means for applying a fluid pressure within the at least one of said two lumens which is closed by said flexible diaphragm means.

12. A probe apparatus according to claim 1, wherein there is only one flexible lumen, further comprising:
at least one earpiece having an isolation diaphragm associated therewith;
conduit means connecting said earpiece to said lumen whereby said pressure variations impinge on said isolation diaphragm; and
flexible diaphragm means for closing the end of said one lumen which is to be inserted into the esophagus.

13. A probe apparatus according to claim 12, further comprising means for applying a fluid pressure within said lumen.

14. A probe apparatus according to claim 12, wherein said lumen comprises a plurality of radially extending holes spaced about its circumference at said end to be inserted into the esophagus; and said diaphragm means comprises a tubular portion extending long and surrounding said lumen at the location of said holes, a pair of radially extending shoulder portions, projecting inwardly from the opposite ends of said tubular portion, whereby said tubular portion is radially spaced from said lumen in the vicinity of said holes, and means for attaching said diaphragm to said lumen.

15. A probe apparatus according to claim 1, wherein there are two lumens, an inner lumen arranged within an outer lumen, said transducer means being responsive to pressure variations transmitted through said inner lumen, further comprising diaphragm means for closing at least the the end of said inner lumen which is to be inserted into the esophagus.

16. A probe apparatus according to claim 15, wherein said outer lumen comprises a plurality of radially extending holes spaced about its circumference in the region of said end of said inner lumen; further comprising seal means extending between said inner lumen and said outer lumen at a location along said outer lumen above said holes; and said diaphragm means comprises a tubular portion extending along and surrounding said outer lumen at the location of said holes, a pair of radially extending shoulder portions projecting inwardly from the opposite ends of said tubular portion, whereby said tubular portion is radially spaced from said outer lumen in the vicinity of said holes, and means for attaching said diaphragm to said outer lumen.

17. An improved double lumen apparatus for use in an esophageal stethoscope, comprising:
a first lumen having a first end for insertion into the esophagus;
a second lumen surrounding said first lumen, said second lumen having a second end for insertion into the esophagus and a plurality of radially extending holes spaced about its circumference and along a portion of its length in the region of said first end;
means associated with said first and second lumens for isolating the interior of said first lumen from the interior of said second lumen, said isolating means extending between said lumens at a location between the ends of said portion of said second lumen; and
flexible diaphragm means for transmitting pressure variations in the esophagus into said first and second lumens, said diaphragm means comprising a tubular portion extending along and surrounding said second lumen at the location of said holes, said tubular section having a reduced diameter portion engaging said second lumen in the region of said isolating means and a pair of radially extending shoulder portions projecting inwardly from the opposite ends of said tubular section to engage said second lumen, whereby said tubular section is radially spaced from said second lumen between said reduced diameter portion and said opposite ends, and means for attaching said diaphragm means to said second lumen.

18. Apparatus according to claim 17, wherein said first lumen surrounds said second lumen and comprises a plurality of radially extending holes spaced about its circumference in the region of said second end and said isolating means extends between said lumens at a location spaced along said first lumen above said holes; and said diaphragm means comprises a tubular portion extending along and surrounding said first lumen at the location of said holes, a pair of radially extending shoulder portions projecting inwardly from the opposite ends of said tubular portion, whereby said tubular portion is radially spaced from said first lumen in the vicinity of said holes, and means for attaching said diaphragm to said first lumen.

19. Apparatus according to claim 17, wherein said isolating means comprises a third lumen having a plurality of radially extending holes spaced about its circumference and along a portion of its length, a first seal means positioned within said third lumen above said holes, said first and second lumens passing sealingly through said first seal means, a second seal means positioned within said third lumen, at a location between the ends of said portion of said third lumen, said first lumen passing sealingly through said second seal means and said second lumen termination between said first and second seal means; and said diaphragm means comprises a tubular portion extending along and surrounding said third lumen at the location of said holes, said tubular portion having a reduced diameter portion engaging said third lumen in the region of said second seal means and a pair of radially extending shoulder portions projecting inwardly from the opposite ends of said tubular portion, whereby said tubular portion is radially spaced from said third lumen between said reduced diameter portion and said opposite ends, and means for attaching said diaphragm to said third lumen.

20. An improved signal processing circuit for use with an esophageal stethoscope of the type including a transducer for producing an electrical signal proportional to the varying frequency and intensity of pressure variations in the esophagus, the transducer having a capacitance, said circuit comprising:
  an amplifer for receiving and amplifying said electrical signal, the input impedance of said amplifier forming a high pass filter with the capacitance of the transducer so that low frequency components attributable to respiratory noises are filtered out;
  means connected to the output of said amplifier for filtering from the amplified signal higher frequency components attributable to heart noises, thereby producing a further, subaudible signal proportional to the cardiac pulse waveform; and
  a source of power operatively connected to said amplifier.

21. An improved circuit according to claim 20, further comprising means connected to the output of said amplifier for filtering from the amplified signal frequency components outside a preselected audible range, thereby producing a signal proportional to cardiac sounds.

22. An improved circuit according to claim 20, wherein low frequency components below approximately 0.1 Hz and higher frequencies above approximately 30 Hz are filtered out.

23. An improved circuit according to claim 21, wherein said preselected audible range is from 70 to 200 Hz.

24. An improved method of monitoring cardiac pulse waveform comprising the steps of:
  inserting a lumen into the esophagus so that the lower end of the lumen is positioned approximately where the aorta crosses the esophagus;
  monitoring pressure variations in said lumen using a transducer which produces an electrical signal proportional to the varying frequency and intensity of the pressure variations in said lumen;
  filtering said electrical signal to remove low frequency components attributable to respiratory noises from the lungs and higher, audible frequencies attributable to heart noises, thereby producing a further, sub-audible signal proportional to the cardiac pulse waveform; and
  displaying the changes in said sub-audible signal with respect to time to provide an indication of cardiac pulse waveform.

25. The method according to claim 24, further comprising the step of positioning said lower end of said lumen approximately where the left ventricle of the heart is closest to the esophagus.

* * * * *